United States Patent [19]

Maryanoff et al.

[11] Patent Number: 4,781,866
[45] Date of Patent: Nov. 1, 1988

[54] PROCESS FOR PRODUCING AMIDINE SULFONIC ACID INTERMEDIATES FOR GUANIDINES

[75] Inventors: Cynthia A. Maryanoff, Solebury Township, Bucks County; James N. Plampin, Roslyn; Robin C. Stanzione, Wayne, all of Pa.

[73] Assignee: McNeilab, Inc., Spring House, Pa.

[21] Appl. No.: 934,376

[22] Filed: Nov. 24, 1986

Related U.S. Application Data

[60] Division of Ser. No. 868,231, May 28, 1986, Pat. No. 4,656,291, which is a continuation-in-part of Ser. No. 711,948, Mar. 15, 1985, Pat. No. 4,656,270.

[51] Int. Cl.$^4$ .................. C07C 139/00; C07D 239/10
[52] U.S. Cl. ...................................... 260/506; 544/141; 546/145; 546/322; 548/351; 549/439; 558/413; 560/142; 540/483; 260/349
[58] Field of Search .............. 544/315; 546/322; 548/317, 322, 351; 558/413; 260/349; 549/506, 439; 560/142

[56] References Cited

U.S. PATENT DOCUMENTS 4,210,658  7/1980  Durant et al. ................. 548/138
4,265,896  5/1981  Durant et al. ................. 546/275
4,381,395  4/1983  Teraji et al. ................. 548/342

FOREIGN PATENT DOCUMENTS 1587258  4/1981  United Kingdom .
178803   2/1966  U.S.S.R. .

*Primary Examiner*—Robert W. Ramsuer
*Attorney, Agent, or Firm*—David J. Levy

[57] ABSTRACT

An efficient synthesis of quanidines, e.g. of the formula (III), by oxidizing a thiourea, e.g. of the following formula (II):

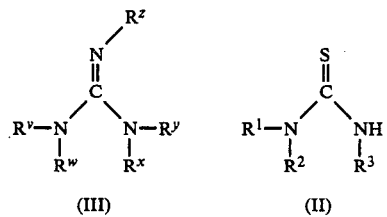

with $H_2O_2$ and a molybdenum catalyst to yield an aminoiminomethane sulfonic acid which can then be reacted with an amine followed by optional transamination steps.

7 Claims, No Drawings

PROCESS FOR PRODUCING AMIDINE SULFONIC ACID INTERMEDIATES FOR GUANIDINES

This application is a division of U.S. Ser. No. 868,231 filed May 28, 1986 now U.S. Pat. No. 4,656,291 which is a continuation-in-part of U.S. Ser. No. 711,948 filed Mar. 15, 1985, now U.S. Pat. No. 4,656,270.

BACKGROUND OF THE INVENTION

As reported in Chemical Week on Sept. 18, 1985 at pages 13—14, there is a considerable need for a simple, inexpensive and non-polluting route to guanidines. Guanidines constitute an important class of organic compounds useful for various medical and agricultural purposes including hypoglycemic agents for the treatment of diabetes.

The present invention also relates to the synthesis of guanidine compounds such as the anti-diabetic compound linogliride or N-(1-methyl-2-pyrrolidinylidene)-N'-phenyl-4-morpholinecarboximidamide and includes synthetic steps and intermediates.

Linogliride fumarate (CAS Registry No. 78782-47-5) is a hypoglycemic compound and is disclosed in U.S. Pat. No. 4,211,867. It is an object of the present invention to provide a high yield, facile and short synthesis of linogliride with by products and reagents which are comparatively safe and easily handled.

At column 11 of U.S. Pat. No. 4,211,867 there is described a method of making a N,N'-disubstituted guanidine intermediate by reacting an N-substituted thiourea with an alkylating agent to produce the corresponding alkylthio compound which is then reacted with an amine to displace mercaptan. Such a route has the disadvantage of removal and disposal of malodorous mercaptans.

Oxidations of thioureas are found in U.S. Pat. Nos. 4,210,658; 4,275,896 and 4,381,395, U.K. Patent No. 1,586,258; U.S.S.R. Patent No. 178,803 published Feb. 3, 1966 and by W. Walter and G. Randau in Liebigs Ann. Chem. 722, pages 98–109 (1969).

SUMMARY OF THE INVENTION

A method has been devised whereby a thiourea is oxidized in high yields to an amidine sulfonic acid by using a molybdenum catalyst such as $Na_2MoO_4$ with $H_2O_2$ as the oxidizing agent. Such sulfonic acids have been found to be excellent intermediates for the preparation of guanidines such as N-phenyl-4-morpholinecarboximidamide, which is itself a precursor for the preparation of linogliride.

DETAILED DESCRIPTION OF THE INVENTION

According to the invention, a thiourea is oxidized with hydrogen peroxide in the presence of a molybdenum catalyst to yield an amidine sulfonic acid. Thus, an acid of the following formula (I):

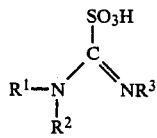

is produced by oxidizing a thiourea of the following formula (II) with $H_2O_2$ in the presence of a Mo catalyst:

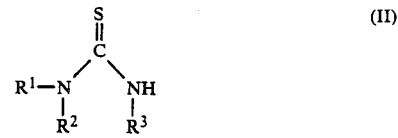

wherein for (I) and (II), $R^1$, $R^2$ and $R^3$ are independently inorganic or organic groups such as hydrogen, $NH_2$, perhaloalkyl, perhaloaryl, $NO_2$ or a saturated or unsaturated alkyl, substituted alkyl, cyclic alkyl, substituted cyclic alkyl, aryl, substituted aryl, heterocyclic or substituted heterocyclic. Preferably, $R^1$ and $R^2$ are both not $NH_2$ or $NO_2$.

As used herein, "alkyl" is any straight or branched hydrocarbon group of the formula $C_nH_{2n+1}$; "cyclic alkyl" is a hydrocarbon group having at least one ring; "aryl" is an aromatic hydrocarbon ring; "heterocyclic" is an aromatic or non-aromatic ring having at least one heteroatom such as N, S or O; and "substituted" is any of such groups where one or more hydrogen atoms are replaced by one or more saturated or unsaturated organic or inorganic groups such as alkyl, cyclic alkyl, aryl, heterocyclic, halogen such as F, Cl, Br or I, $NH_2$, $NO_2$, OH, alkoxy, alkylthio, aryloxy, arylthio, alkanoyl, alkanoyloxy, aroyl, aroyloxy, azido, amido, alkylamino, dialkylamino, arylamino, alkylarylamino, diarylamino, alkanoylamino, alkylsulfinyl, alkylsulfenyl, alkylsulfonyl, alkylsulfonylamido, azo, benzyl, carboxy, cyano, guanyl, guanidino, imino, phosphinyl, phosphorous, silyl, thioxo, ureido or vinylidene or where a carbon atom is replaced by oxygen or sulphur. Such are merely examples of the organic groups which can be used with the invention. Preferably, $R^1$, $R^2$ and $R^3$ contain no moieties which are oxidizable with $H_2O_2$ under mild conditions or, if so, result in a desired group of a higher oxidation state than the starting material. In particular, $R^1$ is hydrogen: or $R^1$ and $R^2$ are hydrogen: or $R^1$, $R^2$ and $R^3$ are hydrogen: or $R^1$ and $R^3$ are hydrogen: or $R^1$ is hydrogen and $R^2$ and $R^3$ are joined to form a $-CH_2CH_2-$ or $-CH_2CH_2CH_2-$ group which may be unsubstituted or substituted.

Amidine sulfonic acids of the formula (I) may be used as intermediates to prepare guanidines by reaction with $NH_3$ or a primary or secondary amine or a cyclic amine having an NH group such as morpholine. The reaction of (I) with the amine may be carried out with a molar excess of the amine neat or in a solvent such as water, acetonitrile or a dipolar aprotic solvent at a temperature up to the boiling point of the solvent, e.g. as described hereinafter for reaction b). Thus, guanidines of the following formula (III):

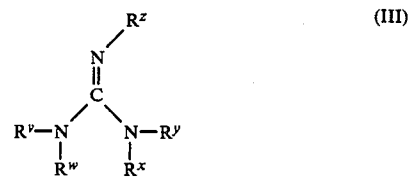

where $R^v$, $R^w$, $R^x$, $R^y$ and $R^z$ are any of the groups described above for $R^1$, $R^2$ and $R^3$ may be prepared according to the invention. Transformations among guanidines may be carried out to achieve the desired substitution as known in the art. For example, if $R^v$ and $R^w$ are hydrogen while alkyl is desired, an alkylation reaction may be carried out. A second reaction is a transamination whereby a given $-NR^vR^w$ group is replaced by another. Other reactions which can be used to introduce various of the R groups in formula (III) are nitration, acylation, cyanation and formylation steps.

The process of the present invention may be employed to prepare guanidine compounds taught in the prior art to have activity, e.g. as $H_2$-antagonists used for the control of gastric acidity and ulcers. References include U.S. Pat. Nos. 3,950,333; 4,013,659; 4,165,377; 4,165,378; 4,242,350; 4,242,351; 4,309,435 and 4,362,728. Many other guanidine compounds are known in the art and specific examples are as follows: these and the previously-cited references being incorporated by reference.

| Identity of $R^1$, $R^2$ or $R^3$ (unless otherwise indicated) | Guanidine Final Product Reference/Utility |
|---|---|
| a. $R^1$ and $R^3$ are independently hydrogen or alkyl and when $R^1 = H$, $R^3$ may be 2-pyridylmethyl which may be substituted in the 6-position by methyl | U.S. Pat. No. 3,352,878 anti-depressant |
| b. 3,5-diamino-6-(H or halo)-pyrazinimidoyl wherein the 5-amino may be substituted by $C_{1-5}$ alkyl (which may be substituted with $C_{1-6}$ cycloalkyl) or lower alkenyl and/or by $C_{1-3}$ alkyl | U.S. Pat. No. 3,449,341 diuretic |
| c. 2-pyrazinoyl having a wide variety of substituents | U.S. Pat. No. 3,472,848 diuretic |
| d. phenoxyalkyl, where the alkyl is $-(CH_2)_2-$, $-CH(CH_3)CH_2-$, $-CH_2CH(CH_3)-$ OR $-(CH_2)_3-$ and the phenyl group may be substituted by halogen, alkoxy, alkyl or nitro | U.S. Pat. No. 4,474,134 hypotensive |
| e. 2-monohalogen-substituted benzyl and 2-methylbenzyl | U.S. Pat. No. 3,506,680 antihypertensive |
| f. $R^1$ and $R^3$ are both phenyl or phenyl substituted by a single $NO_2$, 1 or 2 chloro or 1 or 2 alkyl substituents | U.S. Pat. No. 3,646,029 control soil borne pathogenic organisms |
| g. A benzo[b]thiophen of the formula $(R^*)_m$-benzo[b]-thiophen-$(B)_n$- where $R^*$ is independently halogen, $C_{1-6}$ alkyl or $C_{1-6}$ alkoxy, attached at the 3- or 5- positions of the benzothienyl nucleus; B is $C_{1-4}$ alkylene; n = 0 or 1; and m = 0, 1 or 2. | U.S. Pat. No. 3,855,242 antimicrobial |
| h. $C_{1-8}$ alkyl; $C_{5-8}$ cycloalkyl; adamantyl; phenyl($C_{1-3}$)alkyl; phenyl; or mono- or di-substituted phenyl or phenyl($C_{1-3}$)alkyl where the phenyl moiety is substituted with, same or different, $C_{1-3}$ alkyl, halogen, $CF_3$ or $C_{1-3}$ alkoxy. | U.S. Pat. No. 3,903,084 intermediate (IV)/ antiarrhythmic |
| i. 3-methanesulfonamido-4-hydroxyphenyl or 3-methanesulfonamidophenyl | U.S. Pat. No. 3,903,159 vasoconsrictor |
| j. acetyl; propionyl; or phenyl substituted by $X^1$, $Y^1$ and $Z^1$, where $X^1$ is hydrogen or halo; $Y^1$ is hydrogen, halo, haloloweralkyl, nitro, loweralkyl or loweralkoxy; $Z^1$ is haloloweralkyl, haloloweralkoxy, loweralkylsulfonyl, halo, loweralkoxy, loweralkyl, nitro or cyano, provided $X^1$ and $Y^1$ are not both hydrogen at the same time. | U.S. Pat. No. 3,914,306 anti-hypertensive |
| k. (2,6-dihalophenyl)—CH=N— | U.S. Pat. No. 3,927,096 hypotensives |
| l. (4-(halo,$CH_3$,$CF_3$ or CN)—3—(H or Cl)—phenyl)—CH=N— | U.S. Pat. No. 3,941,825 anti-protozoal |
| m. benzyl or $\beta$-phenethyl | U.S. Pat. No. 3,968,243 antiarrhythmia |
| n. [2-(halo or $CF_3$)—3,4 or 5-(hydrogen, halogen, $CF_3$ or $C_{1-4}$ alkyl)-phenyl]-C(H or $C_{1-4}$ alkyl or $C_{2-4}$ alkenyl or $C_{2-4}$ alkynyl) = N— | U.S. Pat. No. 3,975,533 depression |
| o. 3-(hydroxyl, methyl or hydroxymethyl)-4-hydroxyphenyl | U.S. Pat. No. 4,014,934 vasoconstrictor |
| p. benzyl, p-F—benzyl, p-Cl—benzyl, 2,6-diF—benzyl, m-$CF_3$—benzyl, $-CH_2-C(CH_2CH_2)$phenyl, $-CH_2-C(CH_2CH_2)$—p-F—phenyl, $-CH_2-C(CH_2CH_2)$—p-Cl—phenyl, $-CH_2-C(CH_2CH_2)$—2,6-diF—phenyl, $-CH_2-C(CH_2CH_2)$—m-$CF_3$—phenyl, hydrogen, methyl, ethyl, dimethylaminomethylene or amino. | U.S. Pat. No. 4,107,326 hypotensive, diuretic |
| q. $C_{1-2}$ alkyl | U.S. Pat. No. 4,108,859 microbicides |
| r. (2,6-dimethylphenyl)—CH=N— or (2,6-dichlorophenyl)CH=N— | U.S. Pat. No. 4,154,947 hypotensive, diuretic |
| s. 2-[(4-methyl-5-imidazolyl)-methylthio]-ethyl or straight or branched alkynyl of 3-9 carbons | U.S. Pat. No. 4,157,347 anti-ulcer |
| t. pyrazinecarbonyl with various amino groups at the 3- and 5-positions. | U.S. Pat. No. 4,208,413 |
| u. heterocyclic alkylene where the heterocycle is pyridyl, furyl or thienyl and the alkylene is $-(CH_2)_{1-4}-$; or phenyl substituted by hydrogen, F, Cl, Br, $CF_3$, lower alkyl or lower alkoxy. | U.S. Pat. No. 4,281,004 hypoglycemic |
| v. $NO_2$; or (2-(2-pyridylmethylthio)ethyl or 3-(2-pyridylmethylthio)ethyl having no substitution or hydroxy, cyano, loweralkyl, loweralkoxy, halogen or amino at the 3-position of the pyridyl and/or $-(CH_2)_{1-4}NH_2$, $-(CH_2)_{1-4}NH(loweralkyl)$ or $-(CH_2)_{1-4}N(loweralkyl)_2$ at the 6-position of the pyridyl. | U.S. Pat. No. 4,289,876 anti-ulcer |
| w. phenyl or phenyl-substituted by 1-3, same or different, of lower aliphatic hydrocarbon radicals, hydroxy, mercapto, lower alkoxy, lower alkenoxy, lower alkylenedioxy, lower alkylthio, halo, $CF_3$, $NO_2$, $NH_2$, loweralkylamino, di-loweralkylamino, carboxy or loweralkoxycarbonyl. | U.S. Pat. No. 4,342,764 hypoglycemic |

-continued

| Identity of $R^1$, $R^2$ or $R^3$ (unless otherwise indicated) | Guanidine Final Product Reference/Utility |
|---|---|
| x. any organic substituent | U.S. Pat. No. 4,358,613 phase transfer catalysts |
| y. 2-nitro-4 or 5-($C_{1-6}$ alkylthio)phenyl or a $C_{1-6}$ alkylene terminating with a COOH, $SO_3H$, $OSO_3H$, $PO_3H_2$ or $OPO_3H_2$ group. | U.S. Pat. No. 4,406,893 anthelmintic |
| z. Heterocycle-$(CH_2)_3$NH or Heterocycle-$CH_2$—S—$CH_2CH_2$— where the heterocycle is 4-imidazolyl 5-methyl-4-imidazolyl, 5-ethyl-4-imidazolyl, 5-halo-4-imidazolyl, 2-thiazolyl, 3-isothiazolyl, 4-halo-3-isothiazolyl, 2-pyridyl, 3-halo-2-pyridyl, 3-hydroxy-2-pyridyl, 3-hydroxy-2-pyridyl, 3-methoxy-2-pyridyl or 3-ethoxy-2-pyridyl. | U.S. Pat. No. 4,443,375 antiulcer |
| aa. $R^1$ and $R^3$ combine to form dimethylene or trimethylene | U.S. Pat. No. 4,443,467 antidiarrhea |
| ab. phenoxypentamethylene wherein the phenyl group is subsituted at the 3-position by heterocycle —$CH_2$— where the heterocycle is pyrrolidino, piperidino, hexamethyleneimino, tetrahydropyridino or 4-methylpiperidino, all being attached by the nitrogen. | U.S. Pat. No. 4,491,586 anti-ulcer |
| ac. $R^1$ and $R^2$ may independently be hydrogen, alkyl, haloalkyl, cycloalkyl, aralkyl, alkenyl, aryl, alkynyl, alkoxy, acyl, aroyl, a heterocycle or a substituted heterocycle or $R^1$ and $R^2$ may together for a 3 to 7 atom ring which may include 0 to 2 additional hetero atoms of N, O or S. | U.S. Pat. No. 4,544,670 protozoal infections or gastrointestinal disorders |
| ad. $R^1$ and $R^2$ may independently be hydrogen, alkyl, cycloalkyl, aralkyl, alkenyl, aryl, alkoxy, or a heterocyclic group, or $R^1$ and $R^2$ form a 3 to 7 atom ring which may include 0 to 2 additional heteroatoms of N, O or S. | U.S. Pat. No. 4,565,826 blood pressure lowering |
| ae. hydrogen or methyl | Journal of Medicinal Chemistry, Vol. 10, p. 833–840 (Sept. 1967)/ hypotensive |
| af. hydrogen | J. Med. Chem., Vol. 13, p. 60–63 (Jan. 1970)/ hypoglycemic |

Example of final products which can be synthesized using the step of the present invention are those described in U.S. Pat. No. 3,202,660 including the antihypertensive clonidine. With $R^1$=2,6-dichlorophenyl and $R^2=R^3=H$ in formula (II), the amidine sulfonic acid is reacted with 1,2-diaminoethylene to yield clonidine. Alternatively, if $R^1=H$ and $R^2$ and $R^3$ are —$CH_2CH_2$— in formula (II), the amidine sulfonic acid (I) can be reacted with 2,6-dichloroaniline to yield clonidine. This same compound of formula (I) where $R^2$ and $R^3$ are joined to form a —$CH_2CH_2$— group can be used to synthesize a variety of drugs by reaction with the appropriate amine. Such drugs includes tramazoline, U.K. No. 14304 as described by M. B. Thomas in DE No. 2,538,620 and by D. Cambridge in the European Journal of Pharmacol. 72, 413 (1981), indanozoline as described in U.S. Pat. No. 3,882,229, tiamenidine, St 587 (A. De Jonge et al. in Life Sci. 28, 2009 (1981)) where the amine is 2-chloro-5-trifluoromethylaniline, benclonidine as described in Netherlands Patent 7608971, and flutonidine (see Chemical Abstracts 68 P 39624K (1968)) wherein the amine is 2-methyl-5-fluoroaniline.

Another pharmaceutical which can be prepared is the antiviral moroxydine. Thus, the thiourea $H_2NC(=NH)NHC(=S)NH_2$ is the compound of formula (II) and the corresponding sulfonic acid prepared by the invention process is then reacted with morpholine to yield moroxydine. A general reference for many of such drugs is P. Timmermans et al. in Drugs of the Future, 41 (1984).

Another synthetic route yields the antihypertensive debrisoquin which is formed by first oxidizing thiourea to yield the sulfonic acid (I) where $R^1=R^2=R^3=H$ followed by reaction with 1,2,3,4-tetrahydroisoquinoline. Another antihypertensive drug is guanethidine which may also be formed by reaction of the sulfonic acid (I) where $R^1=R^2=R^3=H$, in this case with 2-(1-N,N-heptamethyleneimino)ethylamine. This same sulfonic acid, also known as aminoiminomethanesulfonic acid, may be used for other mono-substituted guanidines such as guanoxyfen, guanoclor, guanabenz, guanacline, guanazodine, guanisoquin, guanadrel, guanclofine and guanoxan. The single guanidine substituents for each of these, e.g. 1-azacycloloct-2-ylmethyl for guanazodine, and for all other known mono-substituted guanidines are hereby incorporated by reference. From N,N,'-dimethylthiourea starting material of formula (II), one may obtain (methylamino)(methylimino)methanesulfonic acid of the formula (I) where $R^1=H$ and $R^2=R^3=CH_3$, which when reacted with benzylamine yields bethanidine.

A wide variety of $H_2$ blockers contining guanidine units and used to treat stomach ulcers can be prepared according to the invention. A common feature of many of such drugs is an N-substituted cyano (—CN) group which may be attached to the guanidine with cyanogen bromide as described in references such as Japanese Kokai No. 58/92664 (83/92664) to T. Higashikawa and 54/14923 (79/14923) to K. Sirai et al..

It can be seen from the above that a wide variety of guanidines can be prepared with the process of the present invention. Also, the invention can be used to synthesize a sulfonic acid of the formula (I) from the corresponding sulfinic acid.

In particular, N-(1-methyl-2-pyrrolidinylidene)-N'-aryl-4-morpholinecarboximidamides of the formula (VIII), including linogliride, may be prepared according to the following reaction scheme:

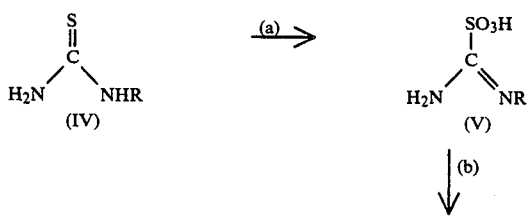

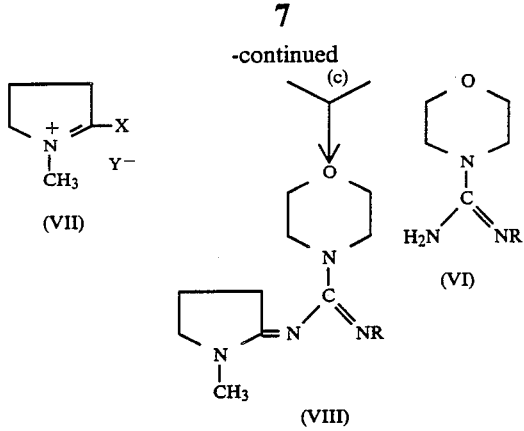

In the above formulae, R is phenyl; methylenedioxyphenyl such as 2,3- or 3,4-methylenedioxyphenyl; phenyl substituted with 1, 2 or 3 substituents independently chosen from the group of halo, such as fluoro, chloro, bromo or iodo, loweralkyl, such as $C_{1-4}$ alkyl including methyl, ethyl and tert-butyl, and lower alkoxy, such as $C_{1-4}$ loweralkoxy including methoxy and ethoxy; or phenyl substituted with a single member of the group consisting of dimethylamino, methylethylamino, diethylamino, loweralkanoylamino such as $C_{1-4}$ alkanoylamino including acetylamino, loweralkylthio such as $C_{1-4}$ alkylthio including methylthio and ethylthio, trifluoromethyl hydroxy, benzyloxy, loweralkanoyloxy such as $C_{1-4}$ alkanoyloxy including acetoxy, lower alkanoyl such as $C_{1-4}$ alkanoyl including acetyl and nitro. Single phenyl substitution may be at the 2, 3 or 4 positions while di- and tri-substitution may be at any available position with di- and tri-substitution of the same moiety being preferred over diverse substitution. In particularly, R is phenyl or phenyl substituted by a fluorine atom, e.g. 4-fluoro, or a methyl group, e.g. 2-methyl.

The compound of formula (VII) is a lactam salt of 1-methyl-2-pyrrolidinone as described in U.S. Pat. No. 4,211,867. The lactam fluoroborates of formula (VII), wherein Y is $BF_4^-$, are generally known and may be obtained according to procedures described in the literature, e.g. see Canadian Pat. Nos. 850,116 and 950,464; U.S. Pat. No. 3,876,658; Ber. 89, Page 2063 (1956); and Org. Synth. 46, 113, 120 (1966). The lactam fluorosulfonates of formula (VII), wherein Y is $OSO_4F^-$, are similarly prepared. In general, 1-methyl-2-pyrrolidinone is reacted with an appropriate trialkyloxonium fluoroborate such as $(CH_3CH_2)_3OBF_4$ or methyl fluorosulfonated to give the corresponding lactam salt. The reaction is preferably carried out from 0° C. to ambient temperature under an inert dry atmosphere (e.g. nitrogen, argon) in an inert anhydrous lower halohydrocarbon solvent such as, for examaple, chloroform, 1,2-dichloroethane, methylene dichloride (most preferred) and the like. Other inert anhydrous organic solvents that may be employed include ethers such as, for example, diethyl ether, dioxane, tetrahydrofuran (THF), 1,2-dimethoxyethane and the like; and aromatic hydrocarbons such as, for example, benzene, toluene, xylene and the like. Alternatively, the corresponding 2-loweralkylthiolactim ethers where X is S-loweralkyl may be prepared by reaction of 1-methyl-2-pyrrolidinone with $P_2S_5$ according to the procedure of R. Gompper and W. Wiser, Org. Syn., Coll. Vol. V, pages 780–783, to yield 1-methyl-2-pyrrolidinethione. Treatment of this thiolactam with loweralkylating agent such as methyliodide, methyl fluorosulfonate, dimethyl sulfate, methyl tosylate, methyl mesylate, and the like, yields the desired 2-loweralkylthiolactim ethers as the corresponding salts. An alternative method of preparing the formula (VII) compounds is by the interaction of 1-methyl-2-pyrrolidinone with dimethyl sulfate to give the corresponding methosulfate salt according to the reaction conditions described by Bredereck et al., Chem. Ber. 96, 1350 (1963). The reaction is preferably carried out in an anhydrous inert organic solvent such as, for example, an aromatic hydrocarbon, e.g. benzene, toluene, xylene and the like, an ether e.g. tetrahydrofuran, dioxane and the like, or a halocarbon, e.g., 1,2-dichloroethane, chloroform and the like. Another method of activating 1-methyl-2-pyrrolidinone is by reaction of the methosulfate salt, i.e., formula (VII) where X is $-OCH_3$ and Y is $OSO_3CH_3^-$ with an alkali metal loweralkoxide, preferably sodium methoxide or sodium ethoxide in the corresponding loweralkanol solvent, according to the reaction conditions described by H. Bredereck, et al., Chem. Ber., 97, 3081–3087 (1964), to yield the corresponding lactam acetal. Another example of an activated lactam of formula (VII) is the chloride salt wherein X is Cl and Y is $Cl^-$. The chloride salts are readily obtained by activation of 1-methyl-2-pyrrolidinone with phosgene (ClCOCl) or thionyl chloride ($SOCl_2$) according to the directions of W. Jentzsch and M. Seefelder, Chem. Ber., 98, 274 (1965), with the evolution of $CO_2$ or $SO_2$, respectively.

In the invention oxidation, thiourea (II), e.g. the N-arylthiourea of formula (IV), in step a), is oxidized to acid (I), e.g. the N-arylformamidinesulfonic acid of formula (V) with hydrogen peroxide in the presence of a molybdenum catalyst, e.g. a molybdenum (VI) catalyst. During the reaction, the oxidation state of the Mo will vary as evidenced by color changes. Thus, when an Mo (VI) catalyst is used as the added catalyst material, the oxidation state will change during the reaction, e.g. (VI) to (III) to (O). The invention comprises all of such molybdenum catalysts. The exact role of each oxidation state in the reaction is not clear. The catalyst to be added is, in particular, a molybdate of the formula $QMoO_4$ wherein Q is two ions having a +1 valence or one ion having a +2 valence. Specific examples of molybdenum catalysts include $H_2MoO_4$, $(NH_4)_2MoO_4$ or $Na_2MoO_4$. Such catalysts include hydrates and other solvates, e.g. $Na_2MoO_4.2H_2O$ and $H_2MoO_4.H_2O$. It has been found that superior yields of final and intermediate products are obtained by conducting the oxidation with a molybdenum (VI) catalyst as opposed to other catalysts which may be considered to be equivalents, e.g. tungsten or chromium. General literature references for similar catalytic systems include: F. Difuria, G. Modena, Rev. Chem. In. (1985) 6, 51; R. A. Sheldon & J. K. Kochi "Metal Catalyzed Oxidations of Organic Compounds" Academic Press, N.Y. 1981; D. DeFilippo, E. F. Trogu, JCS Perkin II (1972) 1500. Hydrogen peroxide is used in the oxidation as an aqueous solution such as 10 to 90% by weight solution, e.g. a 30% solution although other peroxide sources such as peracetic acid can be used.

The oxidation requires slightly more than about 3 equivalents of $H_2O_2$ and the reaction may be carried out at about 0° to 80° C. Preferably, the reaction is carried out in two stages which are:

(i) during addition of the hydrogen peroxide at a temperature of about 0° to 15° C. and (ii) after addition of the hydrogen peroxide at a temperature of about 15° to 80° C.

The oxidation gives the best results when the temperature of the addition of $H_2O_2$ is from about 5° to 10° C. The rate of addition of $H_2O_2$ can usually be increased once about ⅔ of the $H_2O_2$ has been added. During the peroxide addition, it is normal to observe color changes of the reaction mixture from white to green or blue.

After adddition of the $H_2O_2$, the temperature may be allowed to rise by the exotherm of the reaction to a maximum of about 80° C. during which the color will revert to an off-white color. Preferably, the maximum temperature is about 60° C. or most preferably about 40° C. In a modification of this procedure, the first two equivalents of the $H_2O_2$ are added at about 0° to 15° C., the cooling bath is removed and the temperature is allowed to rise to about 20° to 50° C., e.g. about 40° C. with the final equivalent being added at a rate to maintain the temperature at about 40° C.

Sodium chloride or other inert salts may be added to the reaction mixture to prevent freezing.

The starting material thiourea of formula (IV) may be obtained by reaction of the corresponding aryl isothiocyanate with ammonia as described by A. W. Hoffman in J. Fortschrite Chemie 349 (1858) and Comp. Rend., 47 424 as described in Beilstein Hauptwerke, Volume 12, page 454. The arylisothiocyanates of the formula R-N=C=S, many of which are known, may be prepared according to the extensive processes reported in the literature for making isothiocyanates. For example, they may be obtained from the methodologies reported by M. Bogemann et al. in "Methoden der Organische Chemie Houben-Weyl", Eugen Muller (Ed.), Georg Thieme Verlag (Publi.) Stuttgart, Germany, Vol. 9, pages 867–884 (1955); "Preparation des Isothiocyanates Aromatiques" by A. Rasschaert et al., Ind. Chim., Belge, 32, 106 (1967); German Pat. No. 1,300,599; J. Org. Chem., 36, 1549 (1971); U.S. Pat. Nos. 2,395,455 and 3,304,167; French Pat No. 1,528,249; "A New Synthesis of Aliphatic Isothiocyanates", Angew. Chem. Internat. Ed., 6, 174 (1967); Bull. Chem. Soc. Japan, 48 2981 (1975); Tetrahedron. 29, 691 (1973); Chem Ber., 101, 1746 (1968); and J. Indian Chem. Soc. 52, 148 (1975).

In step b), the N-arylformamidinesulfonic acid of formula (V) is reacted with morpholine or an activated form of morpholine such as morpholine acetate. An advantage of the process of the invention compared to the use of the corresponding N-arylformamidinesulfinic acid is that the sulfinic acid ($-SO_2H$) requires that an activated form of morpholine be used, e.g. morpholine acetate, or morpholine with an acid catalyst. This, of course, necessitates an extra synthetic step in the reaction of commercially available morpholine to its activated form or the use of an extra reagent. Thus, a preferred aspect of the invention step (a) is the production of a sulfonic acid which, in the subsequent step (b), allows reaction with the less expensive reactant morpholine. The use of morpholine also results in a higher yield.

The reaction of the sulfonic acid of formula (V) with morpholine may be carried out with a molar excess of morpholine using morpholine itself as the solvent. Thus, use of the sulfonic acid (V) allowing morpholine as the reagent, results in another economy in the overall process. The reaction temperature may be about 15° to 100° C., depending on the particular reactants, with stirring and a co-solvent such as acetonitrile or water may be added to aid such stirring. The co-solvent should be inert to the reactants.

Step (c) is carried out as described in U.S. Pat. No. 4,211,867. In particular, one may use stochiometric quantities of the salt of formula (VII) and the carboximidamide of formula (VI). Suitable anhydrous organic solvents for conducting the reaction include anhydrous aprotic solvents, e.g., ethers, such as, for example, diethylether, tetrahydrofuran, dioxane and the like; lower halogenated hydrocarbons, such as, for example, chloroform, methylene chloride, 1,2-dichloroethane and the like; and aromatic hydrocarbons, such as, for example, benzene, toluene, xylene, and the like. Ambient to 0° C. or higher temperature may be employed depending on the particular reactants. The product (VIII) in the form of the corresponding HY salt, is converted to the corresponding base form, by conventional means, for example, by treatment with a suitable alkali such as alkali metal or alkaline earth metal hydroxides; carbonates and the like. In particular, a temperature of about 25° to 100° C. may be used when the salt (VII) is the methosulfate salt obtained from 1-methyl-2-pyrrolidinone and dimethyl sulfate. Another method of preparing the formula (VIII) compounds is by the interaction of the guanidine precursor (VI) with a chloride salt of formula (VII) in an anhydrous aprotic solvent, such as, for example, an ether, e.g. diethyl ether, dioxane, THF and the like, a halohydrocarbon, e.g. chloroform, methylene chloride, 1,2-dichloroethane and the like, and, preferably, an aromatic hydrocarbon, e.g. benzene, toluene, xylene and the like.

It has surprisingly been found that the reaction of the thiourea (II) or (IV) to yield the amidine sulfonic acid (I) or (V) is assisted by the introduction of ultraviolet visible light or an aliquot of reaction mixture which itself has been subjected to light. In particular, the reaction does occur in the dark — however, a great exotherm is observed. The introduction of light or light-treated reaction mixture minimizes this exotherm. This aspect of the invention was recognized during scaling up work on the reaction of formula (IV) to yield (V) where relatively large volume glass-lined vessels were used in place of the bench-scale work on the reaction which had been done with glass vessels. Such observations are in agreement with the photosensitivity of polyoxometalates recently reported by Craig L. Hill et al. in J. Am. Chem. Soc., 1985, Vol. 197, pages 5148–5157.

In the following Examples and throughout the specification, the following abbreviations may be used: mg (milligrams); g (grams); Kg (kilograms); ml (milliliters); tlc (thin layer chromatography); RT (room temperature); eq (equivalents); L (liter); ir (infrared); m (moles); mmole (millimoles); ~ (about); min (minutes); hr (hours); IPA (isopropyl alcohol); M (molar); N (normal); mp (melting point); bp (boiling point); MeOH (methanol); IPA (isopropanol); EtOH (ethanol); HOAc (acetic acid); and C, H, N, O, etc. (the chemical symbols for the elements). Unless othewise indicated, all temperatures are reported in °C. (degrees centigrade) and, all references to hydrogen peroxide is aqueous hydrogen peroxide and all references to ether are to diethyl ether.

EXAMPLE A i. Formula (V): R=phenyl

N-phenylthiourea (2.0 g, 0.013 m), sodium tungstate dihydrate (0.008 g, 0.00002 m), and sodium chloride (0.25 g), were suspended in water (10 ml) and cooled to 0°-5° C. using an ice/salt bath. Aqueous hydrogen peroxide (4.5 ml, 0.044 m, 30%) was added at a rate to keep the temperature less than 10° C. Once the addition was complete, the ice bath was removed and the reaction was allowed to exotherm to 35° C. and the temperature was controlled between 30°-35° C. with an ice bath. Once the exotherm was complete, the reaction was stirred at ambient temperature for 30 min and then cooled and filtered. The filter cake was washed once with 2 ml of ice water. There was thus obtained 1.47 g of the sulfonic acid of Formula (V) where R=phenyl (56.3%). The ir spectra corresponded to that of desired product.

ii. Formula (VI): R=phenyl

The sulfonic acid product of example Ai (1.46 g) was added to morpholine (1.3 g, 0.015 m) in acetonitrile (9 ml). The reaction exothermed to 35° C. The reaction was then warmed to 50°-60° C. for 30 min. During this time the reaction became homogeneous. The reaction mixture was concentrated and treated with 3N NaOH until very basic. The precipitate was isolated by filtration. There was obtained 1.38 g of the product of Formula (VI) where R=phenyl as a white solid (52%). The white solid was 80.6% pure which translates to a 41.9% yield of pure product.

EXAMPLE 1

This example was conducted in a side-by-side manner with Example A using identical conditions:

a. Formula (V): R=phenyl

N-phenylthiourea (2 g, 0.013 m), sodium molybdate dihydrate (0.005 g, 0.00002 m), and sodium chloride (0.25 g), were suspended in water (10 ml) and cooled to 0°-5° C. using an ice/salt bath. Aqueous hydrogen peroxide (4.5 ml, 0.044 m, 30%) was added at a rate to keep the temperature less than 10° C. Once the addition was complete, the ice bath was removed and the reaction was allowed to exotherm to 35° C. and the temperature was controlled between 30°-35° C. with an ice bath. Once the exotherm was complete, the reaction was stirred at ambient temperature for 30 min then cooled and filtered. The filter cake was washed once with 2 ml of ice water. There was obtained 1.87 g of the sulfonic acid of Formula (V) where R=phenyl (71.6%). The ir spectra corresponded to that of desired product.

b. Formula (VI): R=phenyl

The sulfonic acid product of Example 1a (1.86 g) was added to morpholine (1.3 g, 0.015 m). During the addition the reaction mixture became very thick therefore, acetonitrile (9 ml) was added. The reaction exothermed to 35° C. The reaction was then warmed to 50°-60° C. for 30 min. During this time, the reaction became homogeneous. The reaction mixture was concentrated and treated with 3N NaOH until very basic. The precipitate was isolated by filtration. There was obtained 1.7 g of the product of formula (VI) where R=phenyl as a white solid (65% yield). The yield of pure product, i.e., when adjusted for purity, was 55.6%.

EXAMPLE 2 a. Formula (V): R=phenyl

In a 3-neck round bottom flask (equipped with an ice/salt bath, a thermometer, dropping funnel and a mechanical stirrer), N-phenylthiourea (1520 g, 10.0 m), sodium molybdate dihydrate (10.0 g, 0.04 m), sodium chloride (700 g, 12 m) were suspended in 7000 ml of water and cooled to 0° C. Hydrogen peroxide (30%, 3.6 Kg, 31.8 m) was added dropwise at a rate to maintain the temperature between 0°-15° C. Once the addition was complete, the cooling bath was removed and the reaction was warmed to 15° C. The reaction was then permitted to exotherm to 45° C. at which time a cooling bath was applied to control the exotherm (reaction continued to exotherm to 70° C.). Once the reaction exotherm was complete, the reaction was cooled to about 10° C. and filtered. The filter cake was washed with a small amount of ice water. The sulfonic acid product (V) was obtained as an off-white solid, mp 155°-157° C.

b. Formula (VI): R=phenyl

In a 3-neck round bottom flask (equipped with a mechanical stirrer and a thermometer), morpholine (1040 g, 12 m) was treated with the sulfonic acid prepared in Example 2a. The resulting slurry was stirred for 30-40 min during which time it exothermed to 102° C. If the temperature of the reaction does not reach 100° C., heat should be applied until the reaction temperature is about 100° C. Once the reaction reaches this temperature, the reaction is considered complete. Once the reaction temperature dropped to 50° C., warm water was added and the reaction was treated with charcoal and filtered. The mother liquor was treated with NaOH (50%, 1280 g, 16 m, diluted to 20% with ice). Upon vigorous stirring, a white semi-solid precipitated from the solution. Once the product was filtered, it was dissolved in $CH_2Cl_2$ and any water present was separated. The organic layer was dried over anhydrous $MgSO_4$ and concentrated in vacuo. The mixture was filtered and the filter cake was washed with water. The product was isolated as a white solid in a 56% (1117 g) yield from phenylthiourea. The yield reported is based on the product isolated after the water was removed.

EXAMPLE 3 a. Formula (V): R=phenyl

In a 12 L 3-neck round bottom flask (equipped with an ice/salt bath, a thermometer, dropping funnel and a mechanical stirrer), N-phenylthiourea (734 g, 4.8 m), sodium molybdate dihydrate (5.0 g, 0.021 m), and sodium chloride (260 g, 4.5 m) were suspended in 2.5 L of water and cooled to about 0° C. Hydrogen peroxide (30%, 1710 g, 15.1 m) was added dropwise at a rate to maintain the temperature between 0°-9° C. Once the addition was complete, the cooling bath was removed and the reaction slowly exothermed. The temperature of the reaction was controlled at about 35° C. with a cold water bath. Once the reaction exotherm was complete, the reaction was cooled to 10° C. and filtered. The filter cake was washed with a small amount of ice water. The sulfonic acid product was obtained as an off-white solid in 80% yield (766 g).

b. Formula (VI): R=phenyl

In a 12 L 3-neck round bottom flask (equipped with a mechanical stirrer, a thermometer, and a cooling bath), morpholine (541 g, 6.3 m) in 3.5 L $CH_3CN$ was cooled and treated with glacial acetic acid (378 g, 6.3 m). The resulting slurry was cooled to 10° C. and the sulfonic acid prepared in Example 3a was added in one portion. In contrast to morpholine, the addition of the sulfonic acid to morpholine acetate is endothermic. Once the sulfonic acid was added, the cooling bath was removed.

The reaction warmed to ambient temperature and once all of the solid had gone into the solution, the reaction was complete. The reaction was then concentrated to remove the CH₃CN. NaOH (50%, ~6.3 m) was diluted with 1.5 L of ice and added to the concentrate until the concentrate was neutral. The aqueous mixture was then extracted with ether and the ether phase was discarded. The aqueous phase was then treated with aqueous NaOH until very basic. A white solid precipitate from the solution. The solution was cooled, filtered and washed with water. The product was isolated as a white solid in a 58% yield from phenylthiourea.

EXAMPLE 4 a. Formula (V): R=phenyl

In a 1-liter Morton flask, (equipped with a mechanical stirrer and thermometer, cooled by a water/salt bath) 1-phenyl-2-thiourea (75 g, 0.49 m) and sodium molybdate dihydrate (0.19 g, 0.0008 m) were suspended in 300 ml distilled water and cooled to 0° C. Hydrogen peroxide (113 ml, 1.1 m, 30%) was added dropwise at a rate to maintain the temperature below 5° C. Use of a Morton flask is recommended due to the ease in temperature control it provides. The reaction is initiated with a few milliliters of peroxide; once an exotherm or a color change (white to blue or green) is observed, addition of peroxide may continue. The addition of the first half of the peroxide is very exothermic; however, the addition of the second half is only mildly exothermic. For a successful experiment it is preferred that the temperature not exceed 5° C.; exotherms above about 10° C. result in impurities. Once the addition was complete, the reaction was stirred at 0°–10° C. for an additional 3.5–4.5 hr. The reaction was filtered and the filter cake was washed two times with a small amount of ice water. The acid product was obtained as a lightly colored solid and was used below as a wet cake.

b. Formula (VI): R=phenyl

In a 1-liter 3-neck round bottom flask, morpholine (87.12 g, 1.0 m) in 600 ml acetonitrile was cooled and treated with glacial acetic acid (60.05 g, 1.0 m). The resulting slurry was cooled to about 10° C. and the sulfinic acid product of Example 4a was added in an endothermic reaction. The reaction mixture was stirred and allowed to warm to room temperature overnight. The reaction was checked by tlc (95:5:5; MeOH:CHCL₃:HOAc; silica gel) and cooled to about 0° C. A white solid (morpholine acetate) precipitated and this was isolated by filtration. The filter cake was washed twice with a small amount of cold acetonitrile. The filtrate was concentrated (using a 30° C. bath or cooler) to approximately half the original volume (recovered 450 ml solvent) and then was treated with 25% NaOH until basic. The mixture (add water until all solid is in solution) was extracted 3 times (150 ml each) with methylene chloride; the organic phase was then washed with water (50 ml), dried over anhydrous Na₂SO₄, and concentrated. There were obtained 68 g (68% yield) of product based on phenylthiourea.

EXAMPLE 5

Formula (VIII): R=phenyl (linogliride fumarate)

In a 200 ml round bottom flask, N-methylpyrrolidinone (15.6 g, 0.16 m) was treated with dimethyl sulfate (17.93 g, 0.14 m) and heated on a steam bath for 45 min. The reaction was cooled slightly. N-phenyl-1-morpholine-carboximidamide (14.11 g, 0.068 m) was dissolved in 60 ml hot methylene chloride and added to the complex formed above with stirring. A mild exotherm resulted. The reaction was heated at reflux for half an hour. A check by tlc (silica gel: 95:5:5, MeOH:CHCl₃:HOAc) showed no starting material remained. The reaction was quenched into 250 ml 3N NaOH, extracted 3 times with 50 ml CH₂CL₂, dried over anhydrous K₂CO₃ and concentrated to obtain the free base as a light brown/yellow oil. Fumaric acid (8.6 g, 0.074 m) was dissolved in 90 ml refluxing isopropanol. The free base prepared above was dissolved in 25 ml isopropanol and added to the fumaric acid with vigorous stirring. The solution was stirred and allowed to cool gradually to RT. A white precipitate formed which was collected by filtration. The filter cake was washed 2 times with a small amount of cold isopropanol. The product, linogliride fumarate, was obtained in an 86.5% yield as a white solid, mp 172–175° C., softening at 165° C.

EXAMPLE 6 a. Formula (V): R=4-fluorophenyl 4-fluorophenyl-2-thiourea (2.0 g, 0.0118 m) produced using a modified method of R.L. Frank et al. in Org. Syn., Collected Vol. 8, 735 (1955) and sodium molybdate dihydrate (0.004 g, 0.000016 m) were suspended in 10 ml of water. Hydrogen peroxide (3.6 ml, 30%, 0.035 m) was added dropwise at a rate to keep the temperature between 20°–25° C. Once the addition of the peroxide was complete, the cooling bath was removed and the reaction was allowed to exotherm to 28° C. The reaction was stirred for approximately six hours after which time it was cooled and filtered. The sulfonic acid product was obtained as a gray/brown solid in a 47% yield (mp 150° C., decomposition with gas evolution).

b. Formula (VI): R=4-fluorophenyl

The sulfonic acid product of Example 6a (1.0 g, 0.0046 m) was added to morpholine (0.96 g, 0.011 m) and acetic acid (0.67 g, 0.011 m) in 8 ml acetonitrile at 5° C. The addition was endothermic and upon addition of the sulfonic acid, the reaction mixture turned purple. Within 1–2 min, the reaction turned bright blue. The ice bath was removed and the reaction sat overnight at RT. The reaction was treated with 3N NaOH until very basic then extracted with CHCl₃, the organic phase was dried and concentrated. The resulting green/brown oil crystallized to a solid upon storing at 0° C. The solid was suspended in water and filtered to yield 0.85 g (83% yield from sulfonic acid) of the desired product as a gray solid, mp 100° C. (soft) 105°–108° C. melt.

c. Formula (VIII): R=4-fluorophenyl

N-methylpyrrolidinone (0.38 g, 0.0038 m) was treated with dimethylsulfate (0.38 g, 0.003 m) and heated on a steam bath for 45 min. The guanidine product of Example 6b (0.5 g, 0.0024 m) was dissolved in 5 ml of CH₂Cl₂ with gentle warming and added to the complex formed above. The reaction mixture was stirred without external heat for 1.5 hr (tlc showed reaction complete). The reaction was quenched into 3N NaOH and extracted three times with CH₂Cl₂, dried over anhydrous K₂CO₃ and concentrated. Fumaric acid (0.3 g, 0.0026 m) was dissolved in 7ml refluxing IPA and was treated with the above isolate (dissolved in 3 ml IPA). The fumarate salt was obtained as a white solid in 70% yield (mp 170°–175° C.).

EXAMPLE 7 a. Formula (V): R=2-methylphenyl

2-Methylphenyl thiourea (8.6 g, 0.05 m) and sodium molybdate dihydrate (0.02 g, 0.00008 m) were suspended in 30 ml of water. Hydrogen peroxide (30%, 16 ml, 0.157 m) was added dropwise at a rate to maintain the temperature between 20°-25° C. (cooling bath was used). Once the addition was complete, the reaction exothermed to 28° C. then cooled back to RT. The reaction sat at RT overnight. The reaction was cooled and filtered. The sulfonic acid product was obtained as a light blue solid in a 69% yield (mp 189°-192° C.).

b. Formula (VI): R=2-methylphenyl

The sulfonic acid product of Example 7a (3.0 g, 0.014 m) was added to morpholine (2.4 g, 0.027 m) in 20 ml $CH_3CN$ at RT. The reaction mixture was heated at 45° C. for 1 hr. The reaction was treated with 3N NaOH until very basic and extracted with ether and methylene chloride, dried and concentrated. A clear viscous liquid was obtained which solidified to a white semi-solid. 1.9 g of the desired product was obtained (62% yield).

c. Formula (VIII): R=2-methylphenyl

N-methylpyrrolidinone (1.1 g, 0.011 m) was treated with dimethylsulfate (1.18 g, 0.009 m) and heated on a steam bath for 40 min. The guanidine product of Example 7b (1.5 g, 0.007 m) was dissolved in 10 ml of $CH_2Cl_2$ and added to the complex at RT. The addition was exothermic and the reaction was complete within 0.5 hr. The reaction was quenched with 3N NaOH and extracted 3 times with $CH_2Cl_2$, dried and concentrated. Fumaric acid (0.95 g, 0.008 m) was dissolved in 10 ml refluxing IPA and treated with the isolate (dissolving in 2 ml IPA). The final product was obtained in 48% yield as a white crystalline solid, mp 155°-157° C. with decomposition and gas evolution.

EXAMPLE 8

Formula (I): $R^1=R^2=H$; $R^3=n-C_3H_7$

In a manner similar to Example 4 the sulfonic acid of Formula (I) was prepared where $R^1=R^2=H$ and $R^3=C_3H_7$.

1-Propyl-2-thiourea (1.54 g, 0.013 m), sodium molybdate dihydrate (0.005 g, 0.00002 m), and sodium chloride (0.25 g), were suspended in water (3 ml) and cooled to 0°-5° C. Aqueous hydrogen peroxide (4.5 ml, 0.044 m, 30%) was added at a rate to keep the temperature less than 10° C. Once the addition was complete, the ice bath was removed and the reaction was allowed to exotherm to 40° C. and the temperature was controlled between 35°-40° C. with an ice bath. Once the exotherm was complete, the reaction was cooled to 5° C. and filtered. There was obtained 1.21 g (mp 179°-182° C., dec.) of the sulfonic acid of formula (I) where $R^1=R^2=H$ and $R^3=$n-propyl (56%). The ir spectra corresponded to the S-trioxide derivative.

EXAMPLE 9

Synthesis of Guanethidine 2-(Octahydro-1-azocinyl)ethylamine (0.013 m) is reacted with aminoiminomethanesulfonic acid (0.013 m); the reaction is followed by tlc. After completion of the reaction, the mixture is basified and extracted with methylene chloride several times. The organic phase is dried and evaporated to give the product free base.

EXAMPLE 10

Synthesis of Debrisoquin

Tetrahydroisoquinoline (0.013 m) is treated with aminoiminomethanesulfonic acid (0.01 m) at ambient temperature. After completion of the reaction, it is diluted with acetonitrile, cooled and the solid product is collected by filtration.

EXAMPLE 11

Synthesis of Moroxydine

Amidinothiourea (2.36 g, 0.02 m) was suspended in 5 ml of water. Sodium molybdate dihydrate (0.012 g, 0.00005 m) and about 1.5 g of sodium chloride were added. The solution was cooled to 0° C. and 30% hydrogen peroxide (8.4 ml, 0.08 m) was added dropwise: addition of the first 2.5 ml was very exothermic, dropwise addition required about 45 min. After addition of the second eq, the reaction mixture was allowed to warm to 14°-16° C., at which point the mixture exothermed to 50°-60° C. After cooling to 5° C., the third eq of peroxide was added dropwise; no exotherm was noted. Further cooling afforded a precipitate which was air dried and then placed under high vacuum to give 1.4 g, mp 158°-170° C.

Oxidized amidinothiourea (0.34 g, 0.002 m) is added to morpholine (0.34 g, 0.004 m) and the reaction stirs overnight at ambient temperature. It is checked by tlc (silica gel; 95:5:5: MeOH:HOAc:CHCl$_3$) and allowed to proceed until complete. The reaction mixture is treated with sodium hydroxide, and then is extracted several times with methylene chloride. The organic extracts are combined, dried and concentrated to yield 0.15-0.45 g moroxydine free base.

EXAMPLE 12

Synthesis of Flutonidine

Ethylenethiourea (1.3 g, 0.013 m), sodium molybdate dihydrate (0.0125 g, 0.05 mmol) and sodium chloride (0.5 g) were stirred together in 5 ml water at 0° C. Hydrogen peroxide (30%, 2.6 ml, 0.025 m) was added dropwise at temperatures between $-5°$ C. and 3° C.; color changes were noted throughout the addition. The third eq (1.3 ml) was added to 10°-25° C. The reaction mixture was cooled to 5° C.; a white solid was filtered and dried. The solid (1.45 g, mp 140°-145° C.(d)) was identified spectroscopically as the S-trioxide derivative.

Ethylenethiourea-S-trioxide (0.55 g, 0.0037 m) was added to 5-fluoro-2-methylaniline (0.91 g, 0.0074 m) in 2ml water and 3ml acetonitrile at ambient temperature. The reaction was heated for 2.25 hours at 40°-70° C. The reaction was concentrated, treated with sodium hydroxide and extracted with methylene chloride. The organic extracts were dried and concentrated to yield 0.7 g of an oil which was identified as the title product by spectroscopic methods.

EXAMPLE 13

Synthesis of Clonidine 2,6-Dichlorophenylthiourea (2.87 g, 0.013 m), sodium molybdate dihydrate (0.0125 g, 0.00005 m), and sodium chloride (0.5 g) were stirred together in 5 ml water and cooled to 0° C. In the presence of ordinary laboratory light, hydrogen peroxide (30%, 4.2 ml, 0.04 m) was added dropwise. The first equivalent was added at 5° C.; the second was added between 15°–25° C. and the third was added between RT and 40° C. When the oxidation was complete, the suspension was cooled and the solid was filtered. After drying, the solid (2.7 g, 77%, mp 188°–190° C.(d)) was characterized spectroscopically as the S-trioxide derivative of the starting thiourea.

2,6-dichlorophenylsulfonic acid (1.0 g, 0.0037 m) was added to ethylenediamine (0.5 g, 0.008 m) in the absence of solvent. The reaction exothermed to 35° C. and was diluted with acetonitrile and heated at 65° C. for 7.25 hr. The reaction was concentrated, treated with sodium hydroxide and extracted with methylene chloride. The organic phase was dried and concentrated to yield 0.5 g of clonidine. The product was identified by spectroscopic methods.

What is claimed is:

1. A method for the synthesis of an amidine sulfonic acid of the following formula (I)

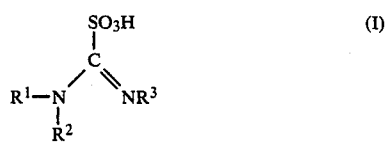  (I)

wherein $R^1$, $R^2$ and $R^3$ are independently hydrogen, $NH_2$, perhaloalkyl, perhaloaryl, $NO_2$, an organic group or are joined to form an organic group, which comprises oxidizing a thiourea of the following formula (II):

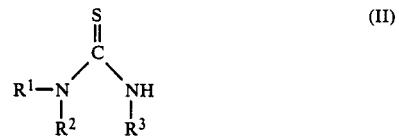  (II)

with hydrogen peroxide by the addition of a molybdenum catalyst of the formula $(NH_4)_2MoO_4$ 2. The method of claim 1, wherein $R^1$ is hydrogen.

3. The method of claim 1, wherein $R^1$ and $R^2$ are hydrogen.

4. The method of claim 1, wherein $R^1$, $R^2$ and $R^3$ are hydrogen.

5. The method of claim 1, wherein $R^1$ and $R^3$ are hydrogen.

6. The method of claim 1, wherein $R^1$ is hydrogen and $R^2$ and $R^3$ are joined to form a substituted or unsubstituted dimethylene or trimethylene group.

7. The method of claim 1, wherein said organic group is alkyl, substituted alkyl, cyclic alkyl, substituted cyclic alkyl, aryl, substituted aryl, heterocyclic or substituted heterocyclic.

* * * * *